(12) United States Patent
Liu et al.

(10) Patent No.: US 10,391,310 B2
(45) Date of Patent: Aug. 27, 2019

(54) FLEXIBLE AND STRETCHABLE ELECTRODES FOR GASTROINTESTINAL IMPLANTS

(71) Applicant: THE REGENTS OF THE UNIVERSITY OF CALIFORNIA, Oakland, CA (US)

(72) Inventors: Wentai Liu, Los Angeles, CA (US); James C. Y. Dunn, Santa Monica, CA (US); Benjamin M. Wu, San Marino, CA (US); Yi-Kai Lo, Los Angeles, CA (US); Chih-Wei Chang, Los Angeles, CA (US); Justin P. Wagner, Los Angeles, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 80 days.

(21) Appl. No.: 15/470,542

(22) Filed: Mar. 27, 2017

(65) Prior Publication Data
US 2017/0266440 A1    Sep. 21, 2017

Related U.S. Application Data

(63) Continuation of application No. PCT/US2015/052725, filed on Sep. 28, 2015.
(Continued)

(51) Int. Cl.
*A61N 1/00* (2006.01)
*A61N 1/36* (2006.01)
(Continued)

(52) U.S. Cl.
CPC ........ *A61N 1/36007* (2013.01); *A61B 5/4233* (2013.01); *A61B 5/4238* (2013.01);
(Continued)

(58) Field of Classification Search
CPC ............ A61N 1/37247; A61N 1/36132; A61N 1/36142; A61N 1/37252; A61N 1/37211;
(Continued)

(56) References Cited

U.S. PATENT DOCUMENTS

| | | |
|---|---|---|
| 5,690,691 A | 11/1997 | Chen |
| 5,995,872 A | 11/1999 | Bourgeois |

(Continued)

FOREIGN PATENT DOCUMENTS

| | | |
|---|---|---|
| WO | 2009094609 A1 | 7/2009 |
| WO | 2011150032 A1 | 12/2011 |
| WO | 2013143603 A1 | 10/2013 |

OTHER PUBLICATIONS

Korean Intellectual Property Office (KIPO), International Search Report and Written dated Jan. 11, 2016, counterpart PCT International Application No. PCT/US2015/052725, pp. 1-12, with claims searched, pp. 13-17.

(Continued)

*Primary Examiner* — Lindsey G Wehrheim
(74) *Attorney, Agent, or Firm* — O'Banion & Ritchey LLP; John P. O'Banion

(57) ABSTRACT

A gastrointestinal stimulation apparatus and methods with an electronic controller and a flexible and stretchable electrode array with a central branch and orthogonal bilateral branches that wrap around a section of the gastrointestinal tract and can accommodate repetitive contraction and relaxation movements of the tract. Array branches have a flexible spring structure, stimulation electrodes, recording electrodes, sensors controlled by a controller and adhesion nodes that fix the branches to the tissue. The electrode array can sense the normal peristalsis from upstream tissue and produce a stimulus signal to stimulate the incapable intestine section to generate stimulation-induced contractions. Electrodes on the incapable intestine section can be used for (Continued)

stimulation or recording, the recorded signal from the incapable intestine section can be sent back to the electronics to form a closed loop control system. An impedance measurement using current stimulation can be used to capture low frequency contraction signals.

18 Claims, 7 Drawing Sheets

Related U.S. Application Data

(60) Provisional application No. 62/057,069, filed on Sep. 29, 2014, provisional application No. 62/144,424, filed on Apr. 8, 2015.

(51) Int. Cl.
*A61F 5/00* (2006.01)
*A61N 1/08* (2006.01)
*A61B 5/00* (2006.01)
*A61N 1/05* (2006.01)

(52) U.S. Cl.
CPC .......... *A61B 5/4255* (2013.01); *A61F 5/0026* (2013.01); *A61N 1/0509* (2013.01); *A61N 1/0517* (2013.01); *A61N 1/08* (2013.01)

(58) Field of Classification Search
CPC .............. A61N 1/36007; A61N 1/0509; A61N 1/0517; A61N 1/08; A61B 5/4233; A61B 5/4238; A61B 5/4255; A61F 5/0025
See application file for complete search history.

(56) References Cited

U.S. PATENT DOCUMENTS

| 7,881,797 B2 | 2/2011 | Griffin |
| 8,364,269 B2 | 1/2013 | Imran |
| 2003/0199955 A1* | 10/2003 | Struble ................ A61N 1/0597 607/119 |

OTHER PUBLICATIONS

Peles, Shachar et al., "Enhancement of antral contractions and vagal afferent signaling with synchronized electrical stimulation", American Journal of Physiology—Gastrointestinal and Liver Physiology, vol. 285, No. 5, pp. G577-G585, Jun. 11, 2003.

European Patent Office (EPO), extended European search report dated Feb. 23, 2018, related European patent application No. 15845840.6, pp. 1-7, claims searched, pp. 8-10.

* cited by examiner

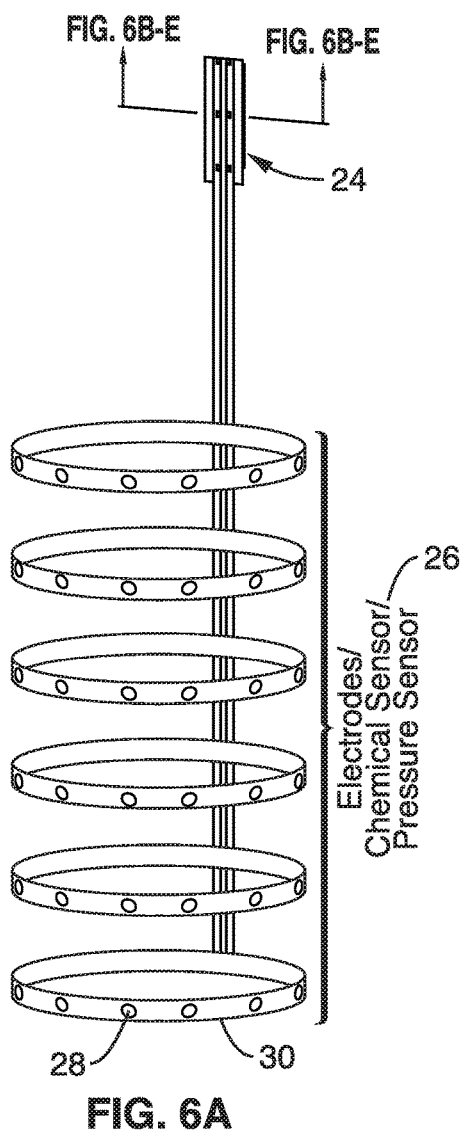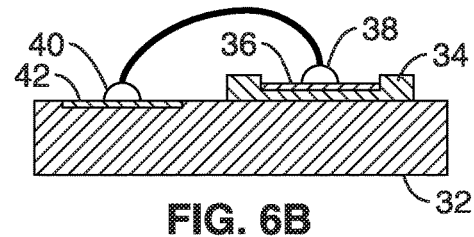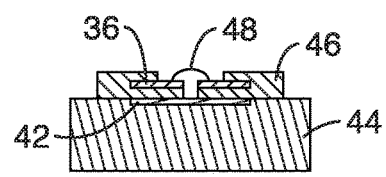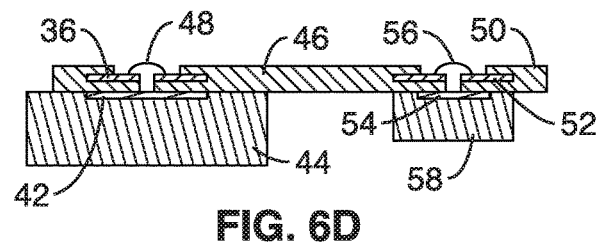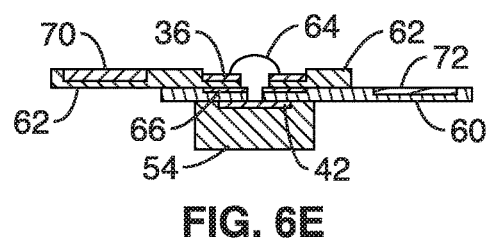

FLEXIBLE AND STRETCHABLE ELECTRODES FOR GASTROINTESTINAL IMPLANTS

CROSS-REFERENCE TO RELATED APPLICATIONS

This application is a 35 U.S.C. § 111(a) continuation of PCT international application number PCT/US2015/052725 filed on Sep. 28, 2015, incorporated herein by reference in its entirety, which claims priority to, and the benefit of, U.S. provisional patent application Ser. No. 62/057,069 filed on Sep. 29, 2014, incorporated herein by reference in its entirety, and which also claims priority to, and the benefit of, U.S. provisional patent application Ser. No. 62/144,424 filed on Apr. 8, 2015, incorporated herein by reference in its entirety. Priority is claimed to each of the foregoing applications.

The above-referenced PCT international application was published as PCT International Publication No. WO 2016/053902 on Apr. 7, 2016, which publication is incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

BACKGROUND

1. Technical Field

The present technology pertains generally to implantable medical devices and methods and more particularly to implantable electrostimulator and sensor devices for monitoring and controlling intestinal peristalsis as a treatment for gastrointestinal disorders.

2. Background

The gastrointestinal system is a complex and essential system of the human body. Consumed food is directed through the stomach and intestines of the system through peristaltic movements. Peristalsis is achieved by a combination of neurological, hormonal, mechanical and chemical mechanisms. The frequency of propagating contractions through the gastrointestinal system is different for the different parts of the system. For example, the contraction propagation frequency in the stomach is approximately three cycles/minute were the small intestines is typically about nine cycles/minute. The timing of the contractions in the intestines is believed to be controlled by sympathetic and parasympathetic neural control circuits that generate the peristaltic waves in the system.

Various diseases, disorders, surgeries, spinal injuries or other trauma can affect the peristaltic activity of the gastrointestinal tract causing the digestive processes to malfunction. Loss of effective peristaltic activity in the gastrointestinal tract can lead to a number of significant clinical conditions. Reduced function or a complete loss of peristaltic function can result in a failure to move the intestinal contents through the digestive tract and material is retained in the intestines. For example, conditions such as paralytic ileus are characterized by distensions of the small intestine from compactions created by segments of intestine with inadequate or non-existent peristaltic activity.

Conversely, over active or excessive peristaltic activity in the whole system or segments of the system can result in the movement of material through the gastrointestinal tract to quickly so that there is not enough time for proper digestion and assimilation and conditions such as colitis. Irregular contraction propagation frequencies or activity over some segments of the digestive tract can influence the peristalsis of other segments.

Some of the conditions of dysfunctional peristalsis can be treated with a variety of medications. However, many of the medications have significant side effects or may be ineffective in treating the cause of the condition only the symptoms. Another approach to treating the irregular or non-functional peristaltic conditions is through electrical stimulation of the nerves or muscles at locations along the intestinal tract to control and regulate the peristaltic activity.

Many different ways of stimulating gastrointestinal function through electrical stimulation have been explored. Electrodes have been placed at various locations in the interior of the gastrointestinal tract such as implantation in the stomach wall or intestinal walls. However, electrodes currently used for electrical stimulation of gastrointestinal tissues are rigid and large in size in order to distribute the energy of the pulse over a large surface area to avoid tissue damage. Large rigid electrodes are susceptible to fatigue failures and separation due to the mechanical stresses created by the peristaltic contractions.

Accordingly, there is a need for gastrointestinal stimulation devices with implantable electrodes that are flexible and durable that will not have fatigue failures or electrode displacement with repeated and significant movements upon stimulation of the targeted tissues.

BRIEF SUMMARY

The technology described herein generally comprises a portable or implantable gastrointestinal stimulator device and system with a flexible and stretchable multiple electrode and sensor array that is applied to sections of the digestive tract and complies with the contraction and relaxation movements of the intestine.

The array preferably has multiple, stimulation electrodes, recording electrodes and optionally other sensors incorporated in a flexible structure that can be adhered to the inner or outer surface of sections of the gastrointestinal tract. The system also has an electronic controller that is preferably programmed to deliver a phased electrical stimulation of sections of the intestines to control and pace the peristaltic movement of material through the gastrointestinal tract, for example.

The electrical stimulation that is controlled by the electronic controller is through the actuation of stimulation electrodes pulsed individually or in groups at selected times. The electronic controller is preferably programmed to sense peristaltic activity and to regulate the pulse, pulse durations, amplitudes, periods, and the sequence of stimulation electrode actuations over time.

Sensors in the array can accurately detect the natural pace or base slow wave rate of the intestine section of the individual patient as well as any peristaltic arrhythmias. The precise detection of the peristaltic activity as a reference will assist in the determination of the need for and the characteristics of the stimulation pulses that are needed to provide normal gastrointestinal flow.

In one embodiment, the stretchable electrode array is wrapped over the intestine along the longitude peristalsis direction and the sensors of the array can sense the spontaneous contraction from the normal intestine. The electric stimulation signal is then sent to the incapable intestine section to produce the contraction based on the recording and analysis of the sensed signal from the normal intestine. In one embodiment, electrodes on the incapable intestine section are used for stimulation or recording, the recorded signal of from the incapable intestine section will be send back to the electronics to form a closed loop control system.

On the other hand, the electrode sensors and electronic controller device can sense the normal peristalsis from the upper stream and produce a stimulus signal to stimulate the incapable intestine section to generate stimulation-induced contraction at a pace that is slower or faster than the natural pace detected by the sensors. If the frequency of the peristaltic contractions is greater than or less than a desired threshold then the electronic controller can adjust the frequency.

In addition, the sensors can sense the strength of the natural peristaltic contractions and the stimulated contractions and provide feedback to the electronic controller regarding the effect of the stimulations. The controller programming can make the decision to increase the pulse strength and frequency as a result of the sensor feedback.

For the recording of peristalsis, a current mode stimulation is used to measure the impedance and uses the impedance to quantify the contraction, in one embodiment. In this embodiment, a gastrointestinal peristalsis measurement method is provided by using current-mode stimulation. Usually, an amplifier with very low high-pass frequency is required to measure the low frequency contraction signal of the intestine. An impedance measurement method using a current stimulation to capture the low frequency contraction signal is preferably used so the amplifier with very low high-pass frequency is no longer needed.

According to one aspect of the technology, a system is provided with an electronic controller and an electrode and sensor array which can sense the spontaneous contractions from the normal intestine and produce a stimulation signal that will produce the contraction based on the recording and analysis of the sensed signal from the normal intestine.

Another aspect of the technology is to provide an electrode array that is flexible and resilient that will not fatigue with repetitive movements of the intestines.

According to another aspect of the technology, an impedance based recording method can be used, which solves the very low frequency contraction signal recording challenge of the intestine.

Further objects and aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWINGS

The technology described herein will be more fully understood by reference to the following drawings which are for illustrative purposes only:

FIG. 6A is a perspective view of a device with a looped electrode with alternative designs that integrate the polymer electrode with the electronics chips, interposer, PCB or other thin film structures.

FIG. 6B is a cross-sectional view of a conventional wire bonded electrode structure.

FIG. 6C is a cross-sectional view of a consolidated embodiment of an electrode structure.

FIG. 6D is a cross-sectional view of an electrode-PCB-IC chip embodiment.

FIG. 6E is a cross-sectional view of an alternative electrode-PCB-IC chip embodiment with two joined substrates.

DETAILED DESCRIPTION

Figure 1:
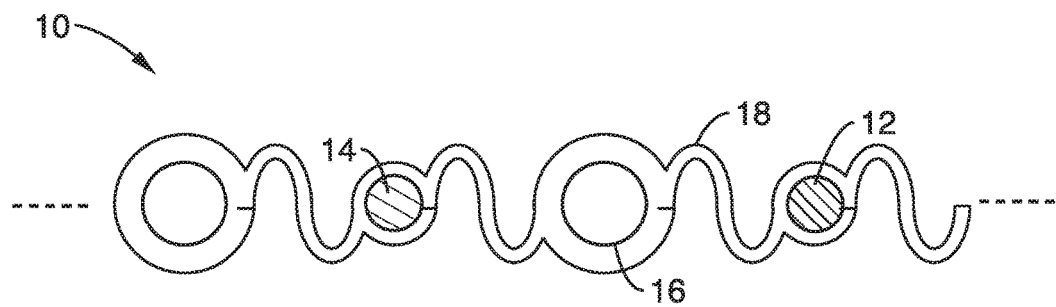
FIG. 1 is a detail view of an electrode depicting spring structures with hollow rings as adhesion nodes according to one embodiment of the technology.

Referring more specifically to the drawings, for illustrative purposes, embodiments of the electrostimulation apparatus and methods for controlled stimulation of peristalsis or other stimulation applications are generally shown. Several embodiments of the technology are described generally in FIG. 1 through FIG. 9D to illustrate the apparatus and methods. It will be appreciated that the methods may vary as to the specific steps and sequence and the apparatus may vary as to structural details without departing from the basic concepts as disclosed herein. The method steps are merely exemplary of the order that these steps may occur. The steps may occur in any order that is desired, such that it still performs the goals of the claimed technology.

Turning now to FIG. 1 through FIG. 4, four different embodiments of sections of an electrode array of the apparatus 10 for controlled electrostimulation are depicted schematically and not to scale. These embodiments are used to illustrate preferred fine electrode structure designs that can form the electrode array of the apparatus illustrated in FIG. 5A, FIG. 6A and FIG. 9A.

One of the key challenges in electrode design is the structure elasticity with good fixture of the device when the device electrodes are implanted onto the tissue. During the contraction of the intestine segment, the deformation of the tissue can include deformations both in- and out-of the electrode plane and therefore the electrode must be able to flex in different directions. Otherwise, the structures fatigue and break apart.

The electrode section embodiments shown in FIG. 1 through FIG. 4 illustrate different flexible structures with repeating units with a stimulation electrode 12, a recording electrode 14 and an adhesion node 16 that are interconnected with a resilient spring structure 18 that allows flexibility and return to the original configuration after flexion.

FIG. 1 illustrates one design of the intestine electrode according to an embodiment 10 of the technology presented herein. The spring structures 18 are utilized to provide more elasticity of extension in every direction, including in both in- and out-of the electrode plane. The enhanced elasticity of the array structure is not only used to fit the curved gastrointestinal tissue surface, but also to make sure the array can stay at the tissue surface during the contraction and peristalsis of the muscle tissue. The elongation and compression capabilities of the array structure should be able to accommodate the maximal movement of the tissue on which the array is implanted.

Figure 2:
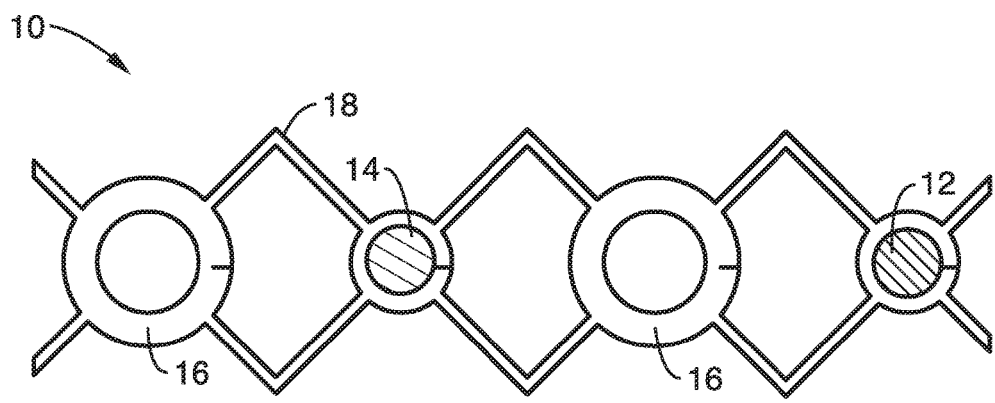
FIG. 2 is a detail view of an alternative embodiment of an electrode showing a spring design that enhances the elasticity of extension in every direction, including in- and out-of electrode plane according to embodiments of the technology.
Figure 3:
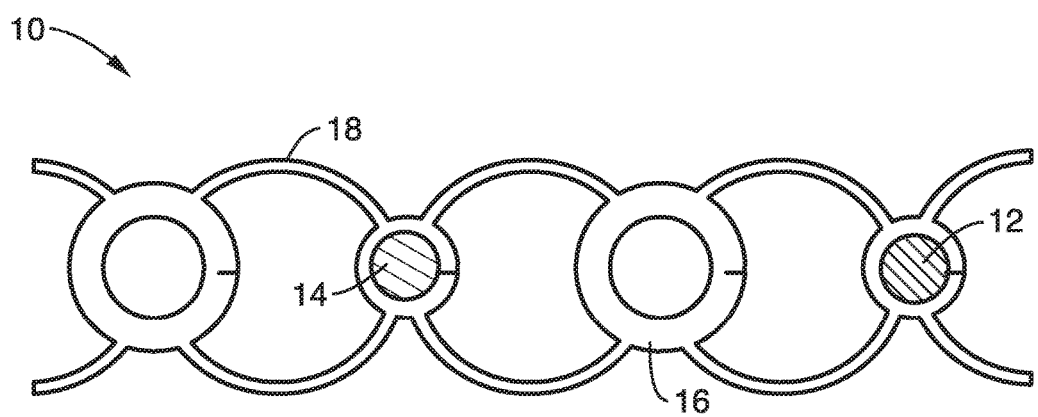
FIG. 3 is a detail view of a second alternative embodiment of an electrode with an alternative adhesion node design structure that will reduce the stress due to the contraction of the intestine.

The spring structure 18 in FIG. 1 is a single structure and interconnects the stimulation electrode 12, recording electrode 14, and adhesion node 16 elements. The unit structures of FIG. 2 and FIG. 3 have elements that are interconnected with two resilient arm structures 18. The spring structures 18 can be angular as shown in FIG. 2 or arcuate as shown in FIG. 3. The adhesion node 16 is larger than the recording 14 and stimulation electrodes 12 in FIG. 1 through FIG. 3. However, the sizes of the electrodes and adhesion nodes can vary.

In one embodiment, some of the recording electrode 14 positions in the array are replaced with other types of sensors such as chemical sensors and pressure sensors. These sensors are connected to an electronic controller and the sensor results obtained over time can be used to determine the stimulation electrode actuation and pulse strength.

Figure 4:
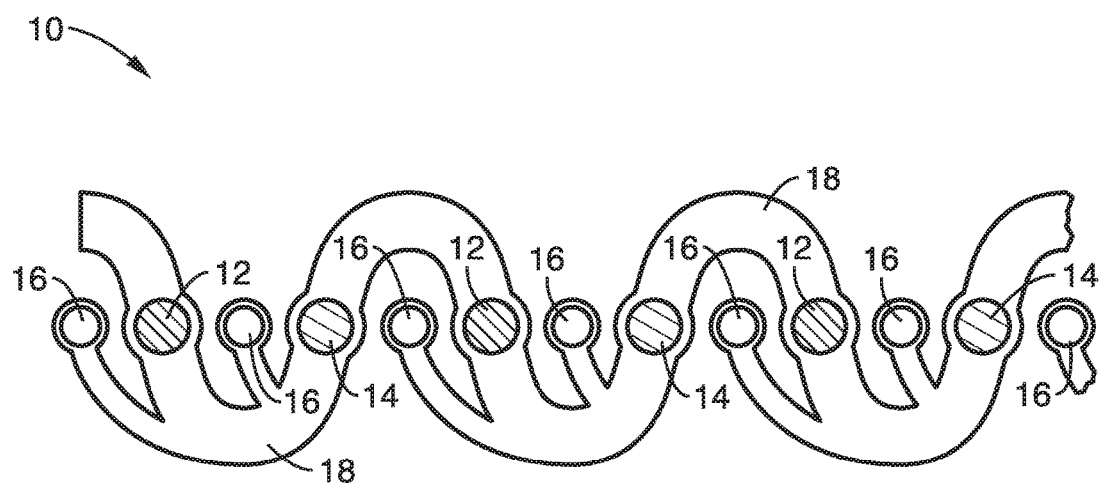
FIG. 4 is a detail view of a third alternative embodiment of an electrode with an alternative adhesion node design structure that will reduce the stress due to the contraction of the intestine.

FIG. 4 shows an alternative adhesion node sine wave design to reduce the stress due to the peristalsis or contraction of the intestine. In this embodiment, the stimulation electrodes 12 and the recording electrodes 14 or other sensors are placed sequentially on the flexible sine wave structure 18. The adhesion nodes 16 in this illustration are on appendages and separate the stimulation electrodes 12 and the recording electrodes 14. However, this sequence of elements in this illustration can be manipulated so that the stimulation electrodes 12 and the recording electrodes 14 are disposed at the ends of the appendages and the adhesion nodes are placed on the sine wave shaped portions of the flexible structure 18, for example. In addition, although the stimulation electrodes 12, adhesion nodes, 16 and the recording electrodes 14 are oriented linearly in FIG. 4, the nodes and electrodes can be placed at a variety of locations along the sine wave structure.

The yield stress of the platinum and polyimide in the design of FIG. 4 was measured to be around 1.5 GPa and 359 MPa. When the stress applied to the structure is higher than the yield stress of the structure, cracks will occur to the structure that will eventually lead to structure failure. COMSOL simulations of the stress due to the normal intestine contraction movement were undertaken. The original design that has adhesion nodes right on the sine polyimide structure shows up to 3.04 GPa which is higher than the yield stress of the structure materials. The modified design moves the adhesion nodes to the side of the sine structure with a linking connection between the sine structure and the adhesion nodes. The stress caused by the intestine movement is reduced to 26.7 KPa, which is in the safe range.

In FIG. 1 through FIG. 5B, the adhesion nodes 16 may be hollow ring structures that are designed for use with either an adhesive (biocompatible epoxy) or a suture to fix the adhesion nodes 16 of the electrode array onto the tissue surface. Adhesion nodes 16 working with an additional biocompatible adhesion epoxy can serve as fixture points on the intestine side wall. Biocompatible adhesive/epoxy is preferred since the electrode array is designed for implantation and repetitive expansions and contractions. The epoxy is preferably applied to the adhesion node 16 in order to glue the hollow ring onto the tissue directly. One of the adapted epoxy examples is poly (ethylene glycol) (PEG), with a known capability in adhesion applications of biomedical devices. In general, the diameter of human small intestine is approximately 2.5 cm to 3 cm. Therefore, the size of the adhesion node and the stimulation/recording electrode should normally not be larger than approximately 1 cm to 2 cm. Multiple adhesion nodes or multiple electrodes can be placed between electrodes or adhesion nodes, respectively.

Figure 9A:
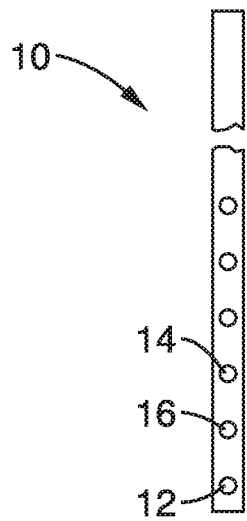
FIG. 9A through FIG. 9D is sequence of diagrams depicting the formation of a thermally annealed helical ribbon structure with electrode structures on the interior side of the ribbon that is configured to wrap around a target tissue such as a section of intestine.

The spring structures illustrated in FIG. 1 to FIG. 4 can be fashioned into electrode arrays of various sizes and designs that can be sized and adapted to specific tissues or tissue segments. Different embodiments of electrode array designs adapted for intestine recording and stimulation are shown in FIG. 5A, FIG. 6A and FIG. 9A.

Figure 5A:
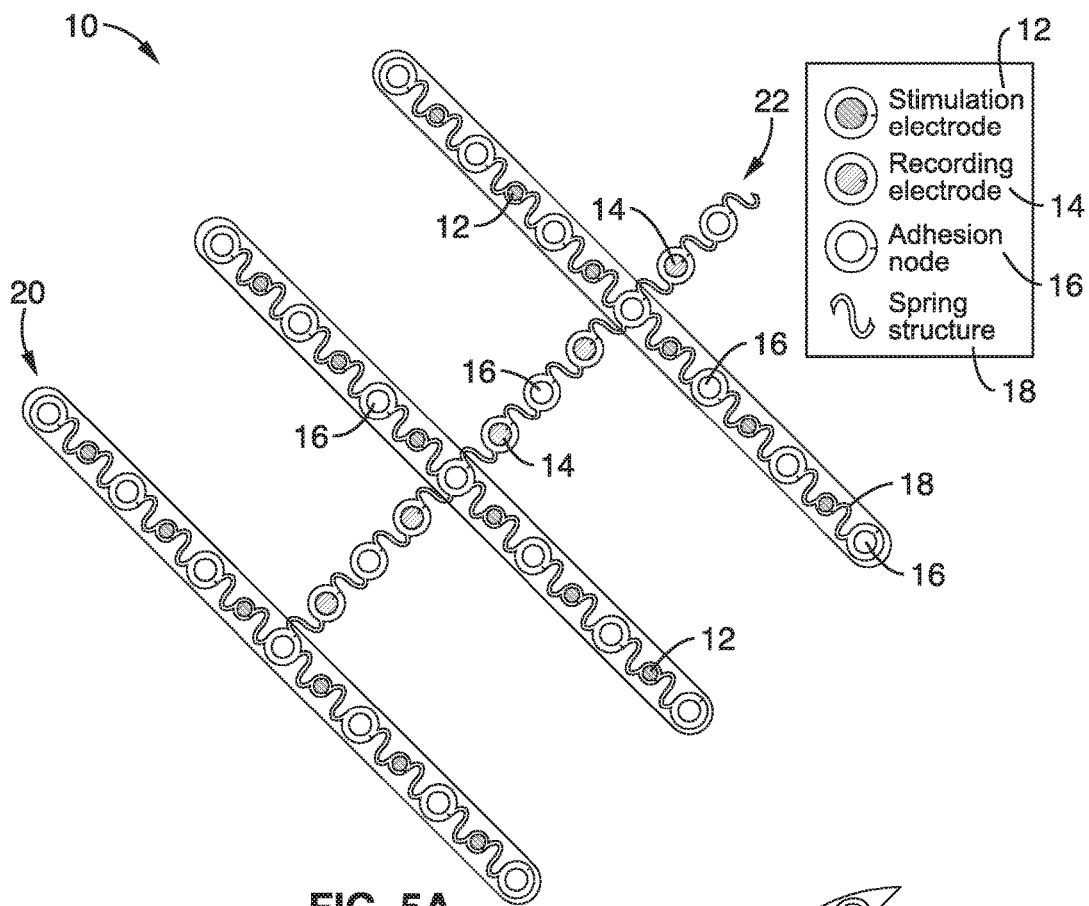
FIG. 5A is a top plan view an electrode array design for intestine recording and stimulation. Spring structures are used to improve the elasticity of the device.
Figure 5B:
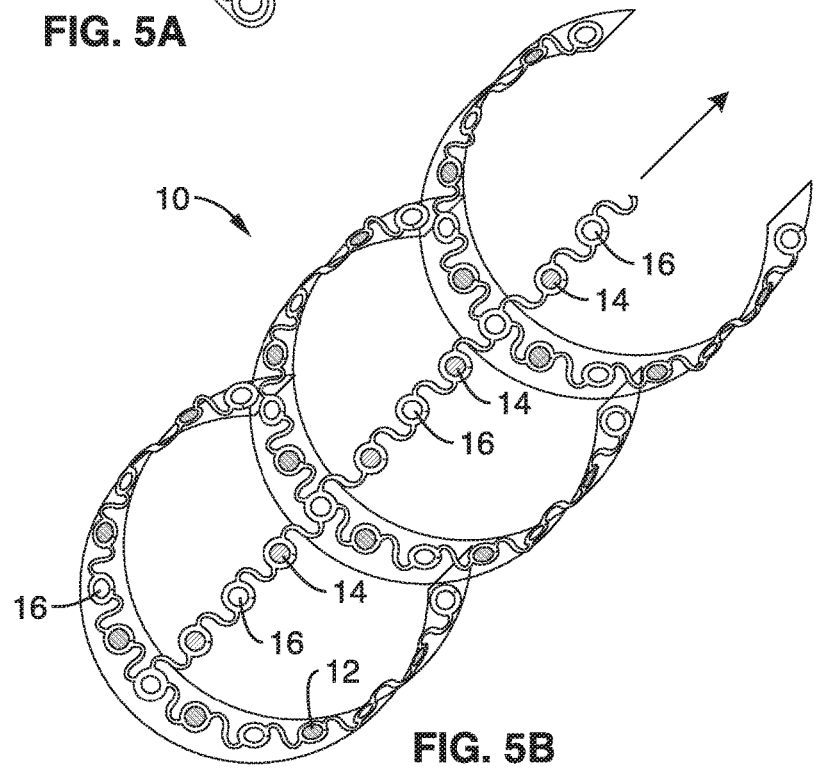
FIG. 5B is a perspective view of an electrode array. The stimulation and recording electrodes are designed on the bilateral branches and central branch, but not limited. The bilateral branches fold over the intestine like a ring, and the central branch will lie along the intestine longitudinally. Adhesion nodes working with an additional biocompatible adhesion epoxy serve as fixture points on the intestine side wall.

FIG. 5A shows the overall design of a gastrointestinal electrode array where the electrode is initially fabricated as flexible planar structure with bilateral branches 20 and central branch 22. The structure is then re-shaped to wrap around the cylindrical shaped intestine or colon and fixed into position as illustrated in FIG. 5B. The stimulation 12 and recording electrodes 14 are designed on the surfaces of the bilateral branches 20 and central branches 22. However, the number of bilateral branches 20 and central branches 22 are not limited. The bilateral branches 20 will be implanted and secured over the intestine like a ring, and the central branch 22 will preferably lie along the intestine longitudinally. Ideally, a dense stimulation electrode array can provide more precise control of the stimulus contraction. Typically, the optimal spacing between the longitudinally wrapped branches 20 will highly depend on the size of the intestine, as well as the effective stimulus induced contraction range. For example, according to prior studies in denervated rat small intestine, only local contraction can be induced by the electrical stimulation with approximately 0.5-1 cm length. Therefore, the spacing between stimulation electrodes for rat should be in the range of several millimeters.

It can be seen that the repeating unit structures, illustrated with the embodiments shown in FIG. 1 through FIG. 4, can be used to form electrode structures with bilateral branches 20 and central branches 22. In the embodiment shown in FIG. 5A and FIG. 5B, the multiple bilateral branches 20 are formed with repeating chain structures of alternating stimulation electrodes 12 and adhesion nodes 16 in a spring structure 18. The central branch 22 in this illustration is formed with repeating chains of unit structures of alternating recording electrodes 14 and adhesion nodes 16 in a spring structure 18. In this embodiment, stimulation occurs with stimulation electrodes 12 in the bilateral branches 20 while the recording occurs in the central branch 22 through the recording electrodes.

In another embodiment, a pre-curved cuff electrode (PCCE) helical design can be used for intestine recording and stimulation as shown in FIG. 9A through FIG. 9D. The PCCE has a pre-curved structure that can wrap the cone-shaped intestine by the residual stress. Therefore, the PCCE will be able to automatically adapt to the size of the intestine within a specific range and no additional adhesion nodes will be needed.

Figure 9B:
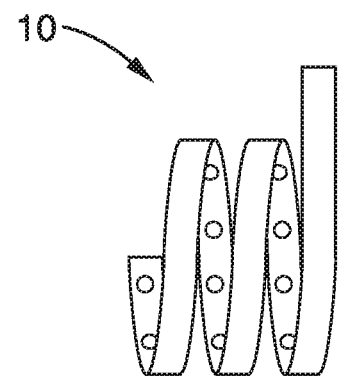
Figure 9C:
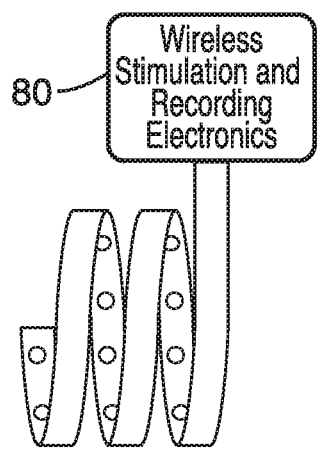

As shown in FIG. 9A through FIG. 9D, patterns of stimulation electrodes 12, recording electrodes 14 and adhesion nodes 16 can be formed on films of any suitable length as seen in FIG. 9A. The patterns can also include sensors in addition to or instead of one or more of the stimulation electrodes 12, recording electrodes 14 or adhesion nodes 16 in the spring structures. The patterns of stimulation electrodes 12, recording electrodes 14 or adhesion nodes 16 on the strips of support film are preferably applied to one side of the film so that these elements are on the interior when wrapped around a mandrel and thermally annealed to fix the helical shape of the structure as shown in FIG. 9B. The shaped strips of electrode/sensor chain structure films can be coupled to wireless stimulation and recording electronics 80 as seen in FIG. 9C. The electronics 80 can be self supporting or can be configured to communicate to devices outside of the body that send and receive commands and data to the apparatus electronics 80.

Figure 9D:
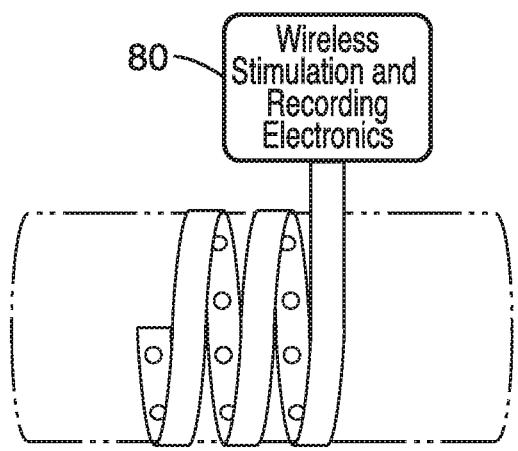

As depicted in FIG. 9D, the fixed flexible structure is resilient and can be unwound and wrapped around a target tissue and the electrodes on the interior of the structure can be brought in contact with the tissue. The electrodes and sensors on the ribbon, rather than discrete rings, provide the stimulation and recording/sensing functions of the apparatus.

The central branches 22 and the leads from the stimulation electrode 12, the recording electrode 14 and any sensors can be joined to an electronic control structure 24 as illustrated schematically in FIG. 6A. Many rings 26 with selected patterned flexible electrodes with stimulation electrodes 28 and recording electrodes 30 along other optional sensors fixed along the circumference of the rings can be used to form arrays that are functionally coupled to control and processing electronics 24.

In the embodiment of FIG. 6A, the apparatus and electrode arrays can be miniaturized for implantation. Alternative controller designs are shown schematically in cross section in FIG. 6B through FIG. 6E. In these embodiments, specially designed bonding pads are used to build the connection between the thin film polymer electrode structure and the electronics chips. In some embodiments, different configurations are used to provide thin structures that can be well tolerated after surgical implantation.

In FIG. 6B, the structure shown is a conventional wire bonded structure. An electrode 34 with a pad 36 is disposed on an interposer (PCB) substrate 32. A second pad 42 is coupled to the pad 36 with a wire metal bump 38 and bump 40.

The alternative structure of the embodiment of FIG. 6C provides a smaller packaging form-factor and flexibility compared to the ordinary wire bonded structure of FIG. 6B. The structure of FIG. 6C has an electrode 46 with bonding pads 36 and 42 disposed on top of each other on an interposer substrate 44. The bonding pads 36 and 42 of the polymer substrate have at least one through-via which is aligned to the bonding pad 42 of the PCB substrate 44, and a ball bump (gold or solder) 48 is placed on pad 36 and the through via by a wire-bonding machine, which creates the electrical and mechanical connection between the polymer substrate and the PCB. Since no extra bonding wires are needed to build the connection, this bonding method can achieve a much smaller form factor.

The embodiment of FIG. 6D, illustrates an alternative approach at building an Electrode-PCB-IC chip bonding. Here the electrode base 46 is joined with the structure of FIG. 6C of bonding pads 36 and 42 disposed on top of each other on an interposer substrate 44 with bump 48 on one section and joined with silicon chips 58 and pads 52 and 54 with ball bump 56 on another section 50 of the electrode 46.

Embodiment of FIG. 6E describes a structure for an electrode bonded with other sensors utilizing multiple polymer substrates coupled to each other. The first substrate 62 has a MEMS structure 70 and pad 36. The second substrate 60 has a second MEMS structure 72 and silicon chips 54 and pad 42. The two substrates 60, 62 and pads 36, 42 and 66 are coupled together with ball bump 64. The silicon chips 54 can be any CMOS circuits, chemical biosensor electrode or physical sensors such as a pressure sensor electrode.

The electrode array and controller generally described in relation to FIG. 5A, FIG. 6A and FIG. 9D above can be implanted and attached to a dysfunctional section of an intestine of a patient, for example. In this illustration, part of the implanted flexible electrode array will cover the part of the normal intestine and other parts of the array will be on non-functional or partly functional tissue, as shown in FIG. 7.

Figure 7:
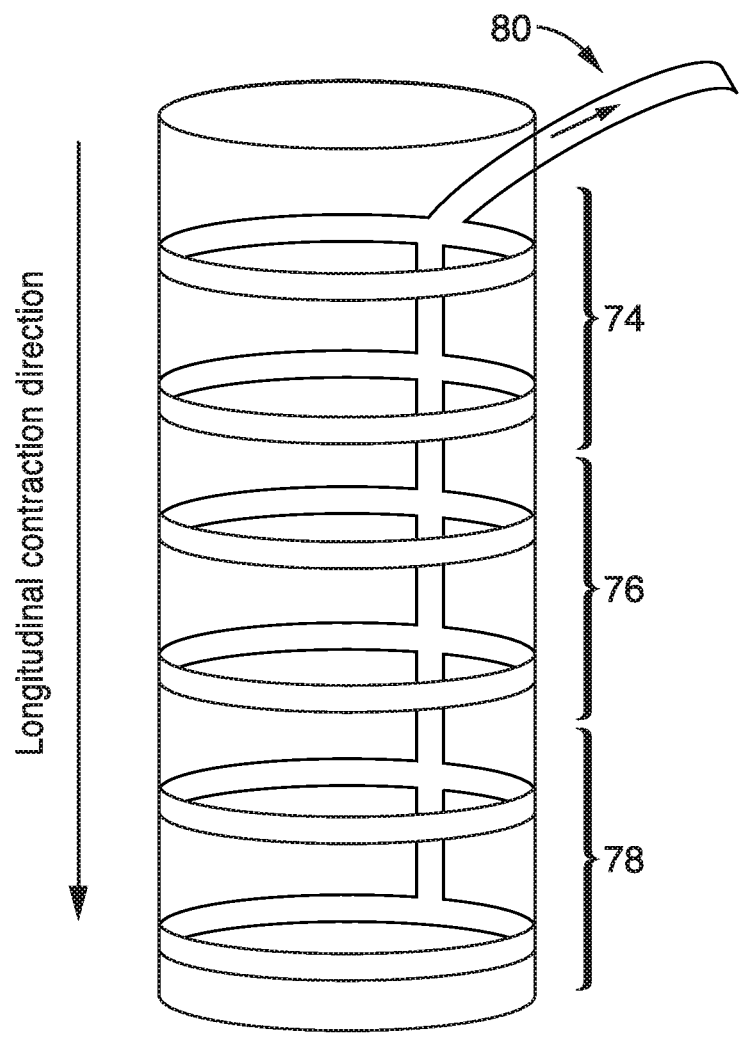
FIG. 7 shows an implantation example according to an embodiment of the technology. The flexible and stretchable electrode covers from the normal and incapable intestine section. The electrodes on the upper normal intestine record the spontaneous peristalsis and send the signal to the electronics to produce the stimulation signal to the electrodes on the incapable intestine section. Note that there are also recording electrodes on the incapable intestine and lower normal sections, which can be used to build a closed loop control system.

The top electrode arms or rings 74 of FIG. 7 are placed on a normally functioning section of the intestine or colon adjacent to the target section of incapable tissue. The recording electrodes or other sensors will sense the normal peristalsis and send produced signals to the electronic controller 80. The arms 74 can have recording electrodes and sensors alone or stimulation electrodes can also be present.

The second set of electrode rings 76 are placed on the incapable section of the intestine or colon. These electrode rings 76 are configured to stimulate the muscle to create contraction propagation and record the induced contraction and send the sensed activity to the controller 80. The controller 80 preferably provides pulses delivered through stimulus electrodes of arms 76 of sufficient intensity and duration to cause a contraction of a desired strength to approximate the normal peristaltic contraction and wave.

The third set of electrode rings 78 of the electrode in this illustration is disposed over the normally functioning intestine or colon at the lower end of the incapable section of the intestine. This set of rings 78 can sense the characteristics of the peristaltic waves that propagate from the stimulated section of the intestine and the results are sent back to the electronic controller 80.

Accordingly, an electrode array installed in this way can have electrode rings 74 on the upper normal intestine record the natural spontaneous peristalsis and then send a signal to the electronic controller 80 to formulate and produce the stimulation signal. The recording electrodes can record the contraction movement waves from the normal intestine from the oral side, and then, sequentially fire stimulation pulses from of the stimulation electrodes in the bilateral rings 76 of the array to generate a contraction wave to continue and mimic the normal intestine peristalsis from the oral to aboral side of the damaged intestinal segment.

The generated wave will again be sensed by both the recording electrodes 76 of the incapable segment and the electrodes 78 lower normal intestine to precisely control the firing timing between each bilateral ring and the stimulation pulse characteristics of the pulse stimuli. By associating peristalsis with the recording and stimulation electrode functions, the stimulus strategy can provide a closed-loop intestinal control system.

Figure 8A:
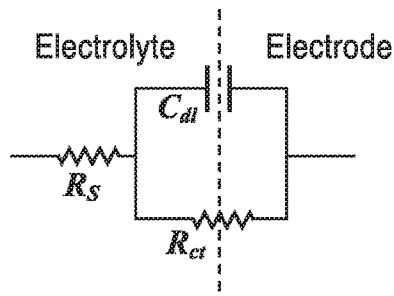
FIG. 8A shows an impedance model of stimulation induced electrode voltage (overpotentials) according to embodiments of the technology.

In one embodiment, the recording electrode records the low frequency intestinal contraction by using impedance analysis. The impedance model is illustrated in FIG. 8A.

Figure 8B:
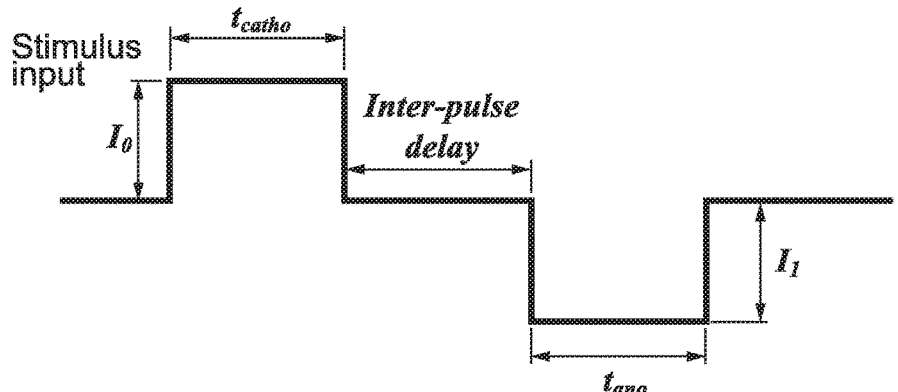
FIG. 8B is a diagram showing square biphasic stimulation input.
Figure 8C:
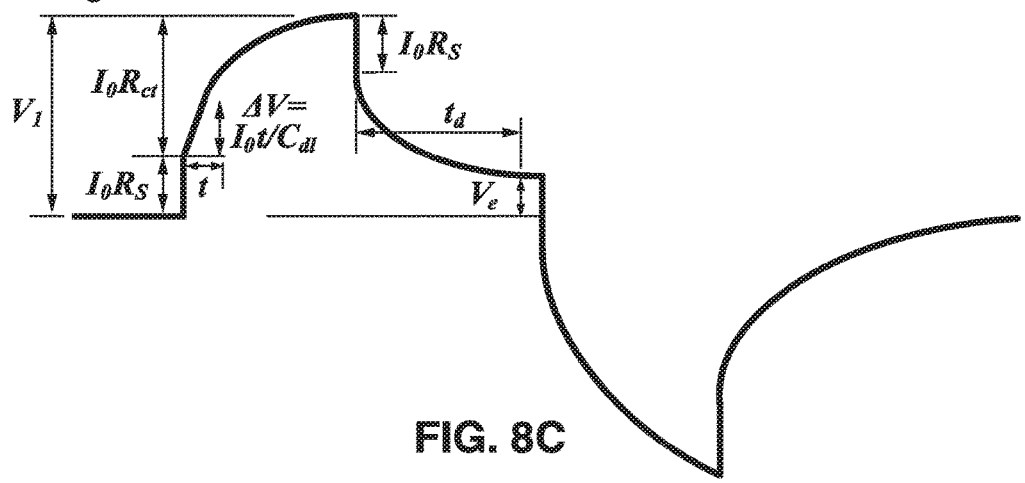
FIG. 8C is a diagram showing the induced electrode voltage.

Electrogastrogram (EGG) records the very low frequency (0.01-0.25 Hz) electrical signals that travel through and control the muscle contractions in gastrointestinal peristalsis. An impedance-based method can be used to record the low frequency signal without using an amplifier with very low high pass filter. When muscles are under contraction, the impedance will change due to the change of volume. The electrode-muscle impedance can be modeled by applying a pulse stimulus current input to electrode and record the induced electrode voltage, as shown in FIG. 8. Alternatively, the recording of the gastrointestinal activity can be accomplished by using biphasic current pulses to acquire the muscle impedance model. A low pass filter or envelop detector can then be used to capture the contraction waveform and differentiate between the contraction waves from the recording. Note that the intensity of the current pulse used for recording is lower than the stimulation threshold to make sure the input pulse for recording will not induce the activation of contraction in this embodiment.

From the description herein, it will be appreciated that that the present disclosure encompasses multiple embodiments which include, but are not limited to, the following:

1. An apparatus for controlling peristalsis of a section of gastrointestinal tract, comprising: (a) a first segment of a resilient electrode array of one or more stimulation electrodes, one or more recording electrodes and one or more adhesion nodes coupled together with flexible spring structures, the first segment configured for adhesion to an upper section of normal gastrointestinal tract; (b) a second segment of a resilient electrode array of one or more stimulation electrodes, one or more recording electrodes and one or more adhesion nodes coupled together with flexible spring structures, the second segment configured for adhesion to a section of incapable gastrointestinal tract; (c) a third segment of a resilient electrode array of one or more stimulation electrodes, one or more recording electrodes and one or more adhesion nodes coupled together with flexible spring structures, the third segment configured for adhesion to a lower section of normal gastrointestinal tract; and (d) a controller coupled to the stimulation electrodes and recording electrodes, the controller configured to produce electrical pulses to the stimulation electrodes and to sense peristaltic activity with the recording electrodes and produce sensed signals; (e) wherein the recording electrodes of the first segment sense normal peristalsis; (f) wherein the recording electrodes of the second and third segments sense electrostimulation contractions; and (g) wherein electric stimulation pulses sent from the controller to the incapable intestine section to produce the contraction are based on recording and analysis of the sensed signals from the recording electrodes of the segments.

2. The apparatus of any preceding embodiment, wherein the resilient electrode array further comprises at least one sensor selected from the group of sensors consisting of a pressure sensor and a chemical sensor.

3. The apparatus of any preceding embodiment, wherein the resilient electrode array further comprises: a plurality of bilateral branches which are shaped to wrap around a cylindrical-shaped intestine or colon; and at least one central branch coupled to the bilateral branches configured to lie along the intestine or colon longitudinally.

4. The apparatus of any preceding embodiment, wherein the bilateral branches of the resilient electrode comprise: chains of repeating units of a recording electrode connected to an adhesion node by a flexible spring structure and the stimulation electrode is connected to the adhesion node by a flexible spring structure; wherein the chain elongates and compresses in a direction along the chain, wherein the chain flexes in an axial direction in relation to an electrode or an adhesion node, and wherein the chain flexes in- and out-of electrode plane.

5. The apparatus of any preceding embodiment, wherein at least one central branch of the resilient electrode further comprise: chains of repeating units of a recording electrode connected to an adhesion node by a flexible spring structure and the stimulation electrode is connected to the adhesion node by a flexible spring structure; wherein the chain elongates and compresses in a direction along the chain, wherein the chain flexes in an axial direction in relation to an electrode or an adhesion node, and wherein the chain flexes in- and out-of electrode plane.

6. The apparatus of any preceding embodiment, wherein the controller is configured to regulate stimulation pulse duration, pulse amplitude, pulse period, and the sequence of stimulation electrode actuations over time.

7. The apparatus of any preceding embodiment, wherein each adhesion node is configured for attachment to a tissue surface with a biocompatible epoxy or a suture.

8. The apparatus of any preceding embodiment, wherein the recording electrodes measure gastrointestinal peristalsis with an impedance measurement using a current stimulation to capture a low frequency contraction signal.

9. The apparatus of any preceding embodiment, wherein the current stimulation is a square biphasic stimulation current input.

10. A flexible electrode apparatus for gastrointestinal implants, the apparatus comprising: a recording electrode; a stimulation electrode; an adhesion node; each the electrode supported by a ring-shaped structure wherein the electrode is centrally located in the ring-shaped structure; the adhesion node comprising a hollow ring-shaped structure; wherein the recording electrode is connected to the adhesion node by a flexible spring structure, wherein the stimulation is electrode connected to the adhesion node by a flexible spring structure, and wherein an electrode to adhesion node to electrode chain is formed; wherein the chain elongates and compresses in a direction along the chain, wherein the chain flexes in an axial direction in relation to an electrode or an adhesion node, and wherein the chain flexes in- and out-of electrode plane.

11. The apparatus of any preceding embodiment, wherein the adhesion node is configured for attachment to a tissue surface using a biocompatible epoxy or suture.

12. The apparatus of any preceding embodiment, wherein the electrodes and adhesion node have a diameter ranging from approximately 1 cm to approximately 2 cm.

13. The apparatus of any preceding embodiment, wherein the electrode chain further comprises at least one sensor selected from the group of sensors consisting of a pressure sensor and a chemical sensor the sensor connected the adhesion node or recording electrode by a flexible spring structure.

14. The apparatus of any preceding embodiment, wherein the chain further comprises: a plurality of chains coupled together to form one or more bilateral branches shaped to adhere to a target tissue; and at least one orthogonal central branch coupled to the bilateral branches.

15. A flexible electrode apparatus for gastrointestinal implants, the apparatus comprising: (a) a first electrode to adhesion node to electrode chain unit; (b) a second electrode to adhesion node to electrode chain unit spaced apart from, and generally parallel to, the first chain unit wherein an intra-chain gap is formed; (c) a third electrode to adhesion node to electrode chain unit spanning the intra-chain gap in a generally orthogonal direction in relation to the first and second chain units; (d) the third chain unit having ends connected to the first and second chain units; (e) wherein each the chain unit comprises: (i) a recording electrode; (ii) a stimulation electrode; (iii) an adhesion node; (iv) each the electrode supported by a ring-shaped structure wherein the electrode is centrally located in the ring-shaped structure; (v) the adhesion node comprising a hollow ring-shaped structure; (vi) wherein the recording electrode is connected to the adhesion node by a flexible spring structure, wherein the stimulation is electrode connected to the adhesion node by a flexible spring structure, and wherein an electrode to adhesion node to electrode chain unit is formed; and (vii) wherein the chain unit elongates and compresses in a direction along the chain unit, wherein the chain unit flexes in an axial direction in relation to an electrode or an adhesion node, and wherein the chain unit flexes in- and out-of electrode plane.

16. The apparatus of any preceding embodiment, wherein the adhesion nodes are configured for attachment to a tissue surface using a biocompatible epoxy or a suture.

17. The apparatus of any preceding embodiment, wherein the electrodes and adhesion nodes having a diameter ranging from approximately 1 cm to approximately 2 cm.

18. The apparatus of any preceding embodiment, wherein the chains form a gastrointestinal electrode having bilateral branches and a central branch which are shaped to wrap around a cylindrical-shaped intestine or colon.

19. The apparatus of any preceding embodiment, wherein the bilateral branches are configured to fit over the intestine or colon like a ring, and the central branch is configured to lie along the intestine or colon longitudinally.

20. The apparatus of any preceding embodiment, wherein the chain unit further comprises at least one sensor selected from the group of sensors consisting of a pressure sensor and a chemical sensor.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An apparatus for controlling peristalsis of a section of gastrointestinal tract, comprising:
   (a) a first segment of a resilient electrode array of one or more stimulation electrodes, one or more recording electrodes and one or more adhesion nodes coupled together with flexible spring structures, said first segment configured for adhesion to an upper section of normal gastrointestinal tract;
   (b) a second segment of a resilient electrode array of one or more stimulation electrodes, one or more recording electrodes and one or more adhesion nodes coupled together with flexible spring structures, said second segment configured for adhesion to a section of incapable gastrointestinal tract;
   (c) a third segment of a resilient electrode array of one or more stimulation electrodes, one or more recording electrodes and one or more adhesion nodes coupled together with flexible spring structures, said third segment configured for adhesion to a lower section of normal gastrointestinal tract; and
   (d) a controller coupled to the stimulation electrodes and recording electrodes, said controller configured to produce electrical pulses to the stimulation electrodes and to sense peristaltic activity with the recording electrodes and produce sensed signals;
   (e) wherein said recording electrodes of said first segment sense normal peristalsis;
   (f) wherein said recording electrodes of said second and third segments sense electrostimulation contractions; and
   (g) wherein electric stimulation pulses sent from the controller to the incapable intestine section to produce the contraction are based on recording and analysis of the sensed signals from the recording electrodes of the segments.

2. The apparatus of claim 1, wherein said resilient electrode array further comprises at least one sensor selected from the group of sensors consisting of a pressure sensor and a chemical sensor.

3. The apparatus of claim 1, wherein said resilient electrode array further comprises:
   a plurality of bilateral branches which are shaped to wrap around a cylindrical-shaped intestine or colon; and
   at least one central branch coupled to the bilateral branches configured to lie along the intestine or colon longitudinally.

4. The apparatus of claim 3, wherein the bilateral branches of the resilient electrode comprise:
   chains of repeating units of a recording electrode connected to an adhesion node by a flexible spring structure and said stimulation electrode is connected to said adhesion node by a flexible spring structure;

wherein said chain elongates and compresses in a direction along said chain, wherein said chain flexes in an axial direction in relation to an electrode or an adhesion node, and wherein said chain flexes in- and out-of electrode plane.

5. The apparatus of claim 4, wherein at least one central branch of the resilient electrode further comprise:
chains of repeating units of a recording electrode connected to an adhesion node by a flexible spring structure and said stimulation electrode is connected to said adhesion node by a flexible spring structure;
wherein said chain elongates and compresses in a direction along said chain, wherein said chain flexes in an axial direction in relation to an electrode or an adhesion node, and wherein said chain flexes in- and out-of electrode plane.

6. The apparatus of claim 1, wherein said controller is configured to regulate stimulation pulse duration, pulse amplitude, pulse period, and the sequence of stimulation electrode actuations over time.

7. The apparatus of claim 1, wherein each adhesion node is configured for attachment to a tissue surface with a biocompatible epoxy or a suture.

8. The apparatus of claim 1, wherein the recording electrodes measure gastrointestinal peristalsis with an impedance measurement using a current stimulation to capture a low frequency contraction signal.

9. The apparatus of claim 8, wherein said current stimulation is a square biphasic stimulation current input.

10. A flexible electrode apparatus for gastrointestinal implants, the apparatus comprising:
a recording electrode;
a stimulation electrode;
an adhesion node;
each said electrode supported by a ring-shaped structure wherein said electrode is centrally located in the ring-shaped structure;
said adhesion node comprising a hollow ring-shaped structure;
wherein said recording electrode is connected to said adhesion node by a flexible spring structure, wherein said stimulation is electrode connected to said adhesion node by a flexible spring structure, and wherein an electrode to adhesion node to electrode chain is formed;
wherein said chain elongates and compresses in a direction along said chain, wherein said chain flexes in an axial direction in relation to an electrode or an adhesion node, and wherein said chain flexes in- and out-of electrode plane; and
wherein said electrodes and adhesion node have a diameter ranging from approximately 1 cm to approximately 2 cm.

11. The apparatus of claim 10, wherein said adhesion node is configured for attachment to a tissue surface using a biocompatible epoxy or suture.

12. The apparatus of claim 10, wherein said electrode chain further comprises at least one sensor selected from the group of sensors consisting of a pressure sensor and a chemical sensor said sensor connected said adhesion node or recording electrode by a flexible spring structure.

13. The apparatus of claim 10, wherein said electrode chain further comprises:
a plurality of chains coupled together to form one or more bilateral branches shaped to adhere to a target tissue; and
at least one orthogonal central branch coupled to the bilateral branches.

14. A flexible electrode apparatus for gastrointestinal implants, the apparatus comprising:
(a) a first electrode to adhesion node to electrode chain unit;
(b) a second electrode to adhesion node to electrode chain unit spaced apart from, and generally parallel to, said first chain unit wherein an intra-chain gap is formed;
(c) a third electrode to adhesion node to electrode chain unit spanning the intra-chain gap in a generally orthogonal direction in relation to said first and second chain units;
(d) said third chain unit having ends connected to said first and second chain units;
(e) wherein each said chain unit comprises:
(i) a recording electrode;
(ii) a stimulation electrode;
(iii) an adhesion node;
(iv) each said electrode supported by a ring-shaped structure wherein said electrode is centrally located in the ring-shaped structure;
(v) said adhesion node comprising a hollow ring-shaped structure;
(vi) wherein said recording electrode is connected to said adhesion node by a flexible spring structure, wherein said stimulation is electrode connected to said adhesion node by a flexible spring structure, and wherein an electrode to adhesion node to electrode chain unit is formed;
(vii) wherein said chain unit elongates and compresses in a direction along said chain unit, wherein said chain unit flexes in an axial direction in relation to an electrode or an adhesion node, and wherein said chain unit flexes in- and out-of electrode plane; and
(viii) wherein said electrodes and adhesion nodes having a diameter ranging from approximately 1 cm to approximately 2 cm.

15. The apparatus of claim 14, wherein said adhesion nodes are configured for attachment to a tissue surface using a biocompatible epoxy or a suture.

16. The apparatus of claim 14, wherein said chains form a gastrointestinal electrode having bilateral branches and a central branch which are shaped to wrap around a cylindrical-shaped intestine or colon.

17. The apparatus of claim 16, wherein the bilateral branches are configured to fit over the intestine or colon like a ring, and the central branch is configured to lie along the intestine or colon longitudinally.

18. The apparatus of claim 14, wherein said chain unit further comprises at least one sensor selected from the group of sensors consisting of a pressure sensor and a chemical sensor.

* * * * *